(12) United States Patent
Kohli et al.

(10) Patent No.: US 9,888,988 B2
(45) Date of Patent: Feb. 13, 2018

(54) DENTAL FLOSS

(75) Inventors: Rajnish Kohli, Hillsborough, NJ (US); Jose Eder Fontana, Sao Paulo (BR)

(73) Assignee: Colgate-Palmolive Company, New York, NY (US)

( * ) Notice: Subject to any disclaimer, the term of this patent is extended or adjusted under 35 U.S.C. 154(b) by 1207 days.

(21) Appl. No.: 12/866,775

(22) PCT Filed: Feb. 6, 2009

(86) PCT No.: PCT/US2009/033305
§ 371 (c)(1),
(2), (4) Date: Aug. 9, 2010

(87) PCT Pub. No.: WO2009/100276
PCT Pub. Date: Aug. 13, 2009

(65) Prior Publication Data
US 2011/0044916 A1    Feb. 24, 2011

Related U.S. Application Data

(60) Provisional application No. 61/027,436, filed on Feb. 8, 2008.

(51) Int. Cl.
| | | |
|---|---|---|
| *A61K 8/72* | (2006.01) | |
| *A61Q 11/00* | (2006.01) | |
| *A61C 15/04* | (2006.01) | |
| *A61K 8/44* | (2006.01) | |
| *A61K 8/49* | (2006.01) | |

(52) U.S. Cl.
CPC ............. *A61C 15/041* (2013.01); *A61K 8/44* (2013.01); *A61K 8/4946* (2013.01); *A61Q 11/00* (2013.01)

(58) Field of Classification Search
USPC ......................................................... 424/357
See application file for complete search history.

(56) References Cited

U.S. PATENT DOCUMENTS

| | | |
|---|---|---|
| 2,667,443 A | 1/1954 | Ashton |
| 3,535,421 A | 10/1970 | Briner et al. |
| 3,678,154 A | 7/1972 | Widder et al. |
| 3,925,543 A | 12/1975 | Donohue |
| 3,932,605 A | 1/1976 | Vit |
| 3,932,608 A | 1/1976 | Anderson et al. |
| 3,943,241 A | 3/1976 | Anderson et al. |
| 3,988,434 A | 10/1976 | Schole et al. |
| 4,011,309 A | 3/1977 | Lutz |
| 4,019,522 A | 4/1977 | Elbreder |
| 4,022,880 A | 5/1977 | Vinson et al. |
| 4,025,616 A | 5/1977 | Haefele |
| 4,042,680 A | 8/1977 | Muhler et al. |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,146,607 A | 3/1979 | Ritchey |
| 4,154,813 A | 5/1979 | Kleinberg |
| 4,160,821 A | 7/1979 | Sipos |
| 2,772,205 A | 2/1980 | King |
| 4,216,961 A | 7/1980 | Curtis et al. |
| 4,225,579 A | 9/1980 | Kleinberg |
| 4,259,316 A | 3/1981 | Nakashima et al. |
| 4,269,822 A | 5/1981 | Pellico et al. |
| 4,305,928 A | 12/1981 | Harvey |
| 4,335,102 A | 6/1982 | Nakashima et al. |
| 4,339,432 A | 7/1982 | Ritchey et al. |
| RE31,181 E | 3/1983 | Kleinberg et al. |
| 4,466,954 A | 8/1984 | Ichikawa et al. |
| 4,477,429 A | 10/1984 | Silbering et al. |
| 4,528,181 A | 7/1985 | Morton et al. |
| 4,532,124 A | 7/1985 | Pearce |
| 4,538,990 A | 9/1985 | Pashley |
| 4,645,662 A | 2/1987 | Nakashima et al. |
| 4,656,031 A | 4/1987 | Lane et al. |
| 4,725,576 A | 2/1988 | Pollock et al. |
| 4,885,155 A | 12/1989 | Parran, Jr. et al. |
| 4,997,640 A | 3/1991 | Bird et al. |
| 5,096,700 A | 3/1992 | Siebel et al. |
| 5,226,434 A | 7/1993 | Britton et al. |
| 5,266,306 A | 11/1993 | Ohtsuki et al. |
| 5,292,526 A | 3/1994 | Gaffar et al. |
| 5,330,357 A | 7/1994 | Keller |
| 5,286,480 A | 8/1994 | Boggs et al. |
| 5,334,617 A | 12/1994 | Ulrich et al. |
| 5,370,865 A | 12/1994 | Yamagishi et al. |
| 5,560,377 A * | 10/1996 | Donovan ............. A61C 15/042 132/321 |
| 5,639,795 A | 6/1997 | Friedman |
| 5,693,795 A | 6/1997 | Friedman et al. |
| 5,747,004 A | 5/1998 | Giani et al. |
| 5,762,911 A | 6/1998 | Kleinberg et al. |

(Continued)

FOREIGN PATENT DOCUMENTS

| | | |
|---|---|---|
| AU | 611544 | 10/1989 |
| AU | 688136 | 3/1998 |

(Continued)

OTHER PUBLICATIONS

US 5,989,525, 11/1999, Kleinberg et al. (withdrawn)
Machado et al. CaviStat Confection Inhibition of Caries in Posterior Teeth, Abstract, 83rd Session of the American Association for Dental Research, Mar. 21-24, (2007), New Orleans, LA.
Chatterjee et al,. Bacterial Acidification and CaviStat Alkalinization of Occlusal Fissure pH, Abstract, 83rd Session of the American Association for Dental Research, Mar. 9-12, (2005), Baltimore, MD.
Kleinberg I., A Mixed-Bacteria Ecological Approach to Understanding the Role of the Oral Bacteria in Dental Caries Causation: An Alternative to *Streptococcus* Mutans and the Specific-Plaque Hypothesis, Crit. Rev. Oral Biol. Med,. 12(2): 108-125 (2002).
Kleinberg I., A New Salvia-Based Anticaries Composition, Dentistry Today, vol. 18, No. 2, Feb. 1999.

(Continued)

*Primary Examiner* — Walter Webb

(57) ABSTRACT

The present invention is directed to a dental floss comprising a basic amino acid or salt thereof.

2 Claims, No Drawings

(56) References Cited

U.S. PATENT DOCUMENTS

| | | |
|---|---|---|
| 5,829,458 A | 11/1998 | Chodorow |
| 5,906,811 A | 5/1999 | Hersh |
| 5,922,346 A | 7/1999 | Hersh |
| 5,997,301 A | 12/1999 | Linden |
| 6,166,102 A | 12/2000 | Ahn et al. |
| 6,217,851 B1 | 4/2001 | Kleinberg et al. |
| 6,270,879 B1 | 8/2001 | Flautt et al. |
| 6,270,890 B1 | 8/2001 | Curtis et al. |
| 6,289,904 B1 | 9/2001 | Suhonen et al. |
| 6,436,370 B1 | 8/2002 | Kleinberg et al. |
| 6,453,912 B1 | 9/2002 | Antler |
| 6,488,961 B1 | 12/2002 | Robinson et al. |
| 6,524,558 B2 | 2/2003 | Kleinberg et al. |
| 6,524,588 B1 | 2/2003 | Kleinberg et al. |
| 6,558,654 B2 | 5/2003 | McLaughlin |
| 6,616,933 B1 | 9/2003 | Breton et al. |
| 6,648,644 B1 | 11/2003 | Flemmig et al. |
| 6,805,883 B2 | 10/2004 | Chevaus et al. |
| 7,083,411 B2 | 8/2006 | Flemmig et al. |
| 2002/0081360 A1 | 6/2002 | Burgard et al. |
| 2005/0006263 A1 | 1/2005 | Tsaur |
| 2005/0048005 A1* | 3/2005 | Stockel ............................ 424/49 |
| 2005/0266382 A1 | 12/2005 | Soler et al. |
| 2006/0246398 A1 | 11/2006 | Groll et al. |
| 2007/0116831 A1 | 5/2007 | Prakash et al. |
| 2007/0119475 A1 | 5/2007 | Hudnall et al. |
| 2007/0154863 A1 | 7/2007 | Cai et al. |
| 2007/0254067 A1* | 11/2007 | Ha ................................ 426/71 |
| 2007/0286820 A1 | 12/2007 | Prencipe et al. |

FOREIGN PATENT DOCUMENTS

| | | |
|---|---|---|
| AU | 703797 | 4/1999 |
| AU | 708978 | 8/1999 |
| AU | 737982 | 9/2001 |
| CA | 2259630 | 1/1998 |
| EP | 485616 | 5/1992 |
| GB | 680250 | 10/1952 |
| JP | 63-288152 | 11/1988 |
| JP | 4036230 A | 2/1992 |
| JP | 6-287126 | 10/1994 |
| JP | H07-100153 A | 4/1995 |
| JP | 7258053 | 10/1995 |
| JP | H07-258053 A | 10/1995 |
| JP | 2001-500405 A | 1/2001 |
| JP | 2001-504083 A | 3/2001 |
| JP | 2003-225250 A | 8/2003 |
| JP | 2005015435 | 1/2005 |
| JP | 2006-206581 A | 8/2006 |
| JP | 2007-506779 A | 3/2007 |
| RU | 2020896 C1 | 10/1994 |
| RU | 2039535 | 7/1995 |
| TW | 504379 | 10/2002 |
| TW | 200509977 | 3/2005 |
| TW | 200640532 | 12/2006 |
| TW | 200744702 | 12/2007 |
| WO | WO2000078270 | 12/2000 |
| WO | WO 03/090639 A1 | 11/2003 |
| WO | WO 2004/113050 | 12/2004 |
| WO | WO2009100267 | 8/2009 |

OTHER PUBLICATIONS

Acevedo et al., "The Inhibitory effect of an arginine bicarbonate/calcium carbonate (CaviStat)-containing dentifrice on the develpoment of dental caries in Venezuelean school children", The Journal of clinical Dentistry, 2005, v.16, No. 3,pp. 63-70, ISSN 0895-8831.

Packaging with ingredient list for DenClude® (launched Dec. 2004).

Packaging with ingredient list for ProClude® (launched Jul. 2002).

Casiano-Colon, et al. "Role of the arginine deiminase system in protecting oral bacteria and an enzymatic basis for acid tolerance", Appl. Environ. Microbiology Jun. 1988, 54(6):1318-1324.

International Search Report and Written Opinion in International Application No. PCT/US09/033305, dated Aug. 28, 2009.

Fujisawa, S. et al., "Application of bis-eugenol to a Zinc Oxide Eugenol Cement," Journal of Dentistry 27 (1999) pp. 291-295.

\* cited by examiner

DENTAL FLOSS

This application claims the benefit of U.S. Patent Application Ser. No. 61/027,436 filed Feb. 8, 2008, the contents of which application is incorporated herein, by reference.

BACKGROUND OF THE INVENTION

The use of dental floss and other interdental cleaners are an important part of dental hygiene, and are used to remove plaque ad other particulate from between the teeth and under the gum line, e.g., areas in the mouth where a toothbrush cannot reach. Frequently, these are the initiation sites of tooth decay, especially if not cleaned regularly. However, even with routine maintenance, caries and gingivitis still develop in these areas. Thus, there is a continuing need to develop more effective dental flosses.

While it is recommended that people floss their teeth at least daily, the reality is that few people floss as often as recommended. Thus there is a need for more effective dental floss compositions for use by occasional flossers.

SUMMARY OF THE INVENTION

It has been discovered that basic amino acids provide beneficial effects in inhibiting bacterial attachment, promoting remineralization of the teeth, reducing the incidence of cavities and dentinal hypersensitivity, and inhibiting cariostatic bacteria in favor of arginolytic bacteria.

The present invention provides a denial floss in combination or association with a composition comprising a basic amino acid or salt thereof, e.g., arginine, arginine bicarbonate, arginine hydrochloride, or arginine phosphate. The basic amino acid or salt may be coated onto the floss, or impregnated within the floss matrix, or the dental floss may be dispensed using a package wherein the floss is stored or dispensed via a chamber comprising a composition comprising a basic amino acid, e.g., any of compositions 1.1-1.15 below.

The invention thus includes a dental floss in combination or association with (e.g., coated or impregnated with) a composition (Composition 1.0) comprising a basic amino acid or salt thereof, e.g, a dental floss in combination or association with any of the following Compositions:

1.1. Composition 1.0 wherein the basic amino acid is arginine, lysine, citrullene, ornithine, creatine, histidine, diaminobutanoic acid, diaminoproprionic acid, salts thereof and/or combinations thereof.
1.2. Composition 1.0 or 1.1 wherein the basic amino acid has the L-configuration.
1.3. Any of the preceding compositions is provided in the form of a salt of a di- or tri-peptide comprising the basic amino acid.
1.4. Any of the preceding compositions wherein the basic amino acid is arginine.
1.5. Any of the preceding compositions wherein the basic amino acid is L-arginine.
1.6. Any of the preceding compositions comprising a physiologically acceptable salt of a basic amino acid.
1.7. Any of the preceding compositions wherein the salt of the basic amino acid is a carbonate.
1.8. Any of the preceding compositions wherein the salt of the basic amino acid is a bicarbonate.
1.9. Any of the preceding compositions wherein the basic amino acid salt is arginine bicarbonate.
1.10. Any of the preceding compositions further comprising fluoride, or a fluoride ion source.
1.11. Any of the preceding compositions comprising a fluoride ion source selected from stannous fluoride, sodium fluoride, potassium fluoride, sodium monofluorophosphate, sodium fluorosilicate, ammonium fluorosilicate, amine fluoride, ammonium fluoride, and combinations thereof.
1.12. Any of the preceding compositions further comprising an antiseptic or antimicrobial.
1.13. Any of the preceding compositions further comprising an antibacterial agent selected from triclosan, herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract, propolis), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.
1.14. Any of the preceding compositions further comprising additional ingredients selected from analgesic agents, anti-inflammatory agents, coagulants, astringents, vitamins, and combinations thereof.
1.15. Any of the preceding compositions further comprising binders, waxes or carriers.

The present invention further comprises a package for storing or dispensing dental floss comprising a chamber containing a basic amino acid, wherein the floss is exposed to the basic amino acid during storage or dispensing, e.g., wherein the chamber contains a composition comprising a basic amino acid, e.g., a composition according to any of compositions 1.0-1.15.

The present invention also encompasses method 2.0, a method to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginoiytic bacteria, (ix) inhibit microbial biofilm formation in the oral cavity, (x) raise and/or maintain plaque pH at levels of at least pH 5.5, (xi) reduce plaque accumulation, (xii) clean the teeth and oral cavity, (xiii) immunize the teeth against cariogenic bacteria, and/or (xiv) reduce erosion, (xv) enhance systemic health, and/or (xvi) treat or inhibit dry mouth, the method comprising flossing the teeth or other surfaces of the oral cavity of a patient in need thereof with a dental floss in combination or association with a basic amino acid in free or salt form (e.g., in combination or association with any of Compositions 1.0-1.15 as hereinbefore described.

Other embodiments of the present invention will be apparent to one of skill in the art.

DETAILED DESCRIPTION OF THE INVENTION

Without intending to be bound by a particular theory, it is believed that basic amino acids in the oral cavity are metabolized by certain types of bacteria, e.g., S. sanguis which are not cariogenic and which compete with cariogenic bacteria such as S. mutans, for position on the teeth and in the oral cavity. The arginolytic bacteria can use arginine and other basic amino acids to produce ammonia, thereby raising the pH of their environment, while cariogenic bacteria metabolize sugar to produce lactic acid, which tends to lower the plaque pH and demineralize the teeth, ultimately leading to cavities. It is believed that use of a Composition of the Invention may lead to a relative increase in the arginolytic bacteria and a relative decrease in the cariogenic bacteria, resulting in a higher plaque pH and a corresponding reduction in the cavitation process.

The basic amino acids which can be used in the compositions of the present the invention include not only naturally occurring basic amino acids, such as arginine, lysine, and histidine, but also any basic amino acids having a carboxyl group and an amino group in the molecule. Accordingly, basic amino acids include, but are not limited to, arginine, lysine, citrullene, ornithine, creatine, histidine, diaminobutanoic acid, diaminoproprionic acid, salts thereof or combinations thereof. In a particular embodiment, the basic amino acids are selected from arginine, citrullene, and ornithine, preferably, arginine, for example, 1-arginine.

The compositions of the invention are used in the mouth, so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion. A preferred salt is a bicarbonate, e.g., arginine bicarbonate.

Methods of manufacturing dental floss are well known in the art. For example, dental floss may be produced from nylon, as nylon salt is polymerized and the resulting polymer is pumped or extruded to form monofilaments. The filaments are allowed to harden, and then combined to form a strand of floss. Dental floss may be produced from polytetrafluoroethylene (PTFE or Teflon®), polypropylene, polyethylene, styrene butadyene copolymers, combination of them. The polymer is melted and extruded into thin strands. See also U.S. Pat. No. 6,270,890, the contents of which are herein incorporated by reference.

In one embodiment, resin, e.g., nylon or PTFE, is mixed with a basic amino acid, or a salt thereof, and extruded to form a filament (e.g., in the case of nylon) which are twisted to form the floss, or formed into a single ribbon of floss (e.g., in the case of PTFE). It should be understood that some of the basic amino acid or salt will be disposed near the surface of the floss, and will be exposed and released when the dental floss is used. In one embodiment, the floss has a denier of about 450 to about 1350. In another embodiment the dernier of the floss is from about 100 to about 900.

Method for coating dental floss is also known in the art. In one embodiment of the present invention, the dental floss is treated in an emulsion bath comprising arginine or a pharmaceutically acceptable salt thereof. The emulsion bath may optionally contain one or more waxes, which adhere to the floss, and thereby cause the arginine to adhere to the floss. In another embodiment, a dental floss comprising a non-PTFE fiber is coated with a first and a second coating overlaying the first coating. The first coating is a nylon bonding coating, and the second coating is a wax or polymer, e.g., such as polyvinyl alcohol, polyvinyl acetate, etc, in combination or association with a basic amino acid or salt thereof. See e.g., U.S. Pat. No. 6,289,904, herein incorporated by reference.

The floss may be in the form of a single ribbon (e.g., a Teflon® or polyethylene ribbon). Alternatively, it may be bundle of thin filaments, e.g., nylon filaments. The number of filaments will be from about 2 to about 300, e.g., from about 2 to about 200, depending on the denier of the filaments. The filaments are twisted with about 1 to 5 twists per inch to form the floss. The twisting provides integrity of the floss on the spool and during subsequent handling. However, when used the filaments will spread out and splay against tooth surfaces. The floss may also be formed of interlocking fibers, e.g., as in the case Oral-B Ultra Floss™. In any case the final floss product is preferably of a thickness that allows it to fit between the teeth. The floss may be coated with a wax. Where multiple filaments are used, the coating may applied before or after twisting, preferably after twisting. Other additives may be applied to a wax coated floss after the wax coating. The flavor can be applied as a liquid or a solid. It is preferred to use a spray dried solid. Likewise, the various other additives can be applied as a liquid or a solid. When applied as a liquid the floss is dried prior to being wound onto a spool. The drying can be by radiant drying or air drying. After drying, the floss is wound onto a spool.

Denial floss is commonly supplied in plastic dispensers that contain 10 to 50 meters of floss. The dispenser typically has a small protected blade used to sever the floss when a desired amount is pulled out.

In one embodiment, of the present invention, a denial floss dispenser is provided which contains a basic amino acid, salt, or solution thereof is disposed within the container and in contact with the floss. As the floss is stored or as a user pulls out a desired amount of floss, the floss comes in contact with the basic amino acid, salt, or solution, thereby coating the floss.

Various devices have been developed to aid a user in flossing their teeth, especially when flossing of the particular tooth is difficult or awkward. Such devices are shaped like wands to hold the floss. The present invention contemplates the use basic amino acids and their salts in combination with such devices. Additionally, dental floss that do not contain a basic amino acid or salt and retained on such wands may be dipped into a basic amino acid, salt, or solution thereof to take advantage of the present invention.

In one embodiment of the present invention, the dental floss may optionally include fluoride, or a fluoride ion source. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat.

No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

The dental floss of the present invention may also comprise abrasive particles, e.g., aluminium oxide, small particle silica, or other abrasive or polishing particles. See e.g., U.S. Pat. No. 6,453,912, incorporated herein by reference.

The dental floss of the present invention may also comprise an antiseptic or antimicrobial selected from triclosan, herbal extracts and essential oils (e.g. rosemary extract, thymol, menthol, eucalyptol, methyl salicylate), bisguanide antiseptics (e.g., chlorhexidine, alexidine or octenidine), quaternary ammonium compounds (e.g., cetylpyridinium chloride), phenolic antiseptics, hexetidine, povidone iodine, delmopinol, salifluor, metal ions (e.g., zinc salts, for example, zinc citrate), sanguinarine, propolis, and combinations thereof to further aid in the beneficial effects of the basic amino acid.

As use of dental floss may cause discomfort or bleeding during or after use, it may optionally comprise analgesic agents, anti-inflammatory agents, coagulants, vitamins, and combinations thereof.

The invention claimed is:

1. A dental floss consisting of a polymer; and
   a composition consisting of arginine or a physiologically acceptable salt of arginine, wherein the polymer consists of nylon and the polymer is coated or impregnated with said composition; and
   the dental floss has a denier in the range selected from the group consisting of about 450 to about 1350 and about 100 to about 900.

2. The floss of claim 1 wherein the physiologically acceptable salt of arginine is arginine bicarbonate.

* * * * *